United States Patent

Chambers et al.

[11] Patent Number: 5,968,890
[45] Date of Patent: *Oct. 19, 1999

[54] CLEANSING COMPOSITION CONTAINING POLYETHYLENE GLYCOL

[75] Inventors: John George Chambers, Wirral, United Kingdom; Izuma Kutsuwa, Chiba Prefecture, Japan; David Serridge, Wirral, United Kingdom

[73] Assignee: Lever Brothers Company, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/818,192

[22] Filed: Mar. 14, 1997

[30] Foreign Application Priority Data

Apr. 17, 1996 [GB] United Kingdom .................. 9607963

[51] Int. Cl.$^6$ ............................ C11D 17/00; C11D 9/00; A61K 7/045
[52] U.S. Cl. ..................... 510/426; 510/124; 510/125; 510/127; 510/427; 510/428; 510/432; 510/502
[58] Field of Search ...................... 510/119, 123, 510/124, 125, 127, 130, 426, 427, 428, 432, 499, 501, 502; 424/70.19, 70.21, 70.24, 70.31

[56] References Cited

U.S. PATENT DOCUMENTS

| 5,523,025 | 6/1996 | Erilli | 510/417 |
| 5,529,723 | 6/1996 | Drapier | 510/417 |
| 5,580,848 | 12/1996 | Drapier | 510/417 |
| 5,604,195 | 2/1997 | Misselyn et al. | 510/400 |
| 5,696,073 | 12/1997 | Jakubicki et al. | 510/417 |

FOREIGN PATENT DOCUMENTS

| 0197480 | 10/1986 | European Pat. Off. . |
| 0461593 | 12/1991 | European Pat. Off. . |
| 0485212 | 5/1992 | European Pat. Off. . |
| 1499746 | 2/1978 | United Kingdom . |
| 2172298 | 9/1986 | United Kingdom . |
| 2192404 | 1/1988 | United Kingdom . |
| 2297975 | 8/1996 | United Kingdom . |
| 91/11984 | 8/1991 | WIPO . |
| 92/05234 | 4/1992 | WIPO . |
| 93/19149 | 9/1993 | WIPO . |
| 97/01328 | 1/1997 | WIPO . |

OTHER PUBLICATIONS

International Preliminary Examination Report mailed Feb. 25, 1998.
International Serach Report application No. PCT/EP 97/00893 mailed Jun. 27, 1997.
Search Report from the UK dated Jul. 11, 1996.

*Primary Examiner*—Necholus Ogden
*Attorney, Agent, or Firm*—Ronald A. Koatz

[57] ABSTRACT

An aqueous liquid detergent composition comprises a mixture of synthetic anionic and amphoteric surfactants in a weight ratio within the range 4:1 to 0.1:1 and a polyethylene glycol having a molecular weight of not more than 100,00. The later component boosts the lather of the composition during use. It may also enhance the mildness of the formulation.

4 Claims, No Drawings

CLEANSING COMPOSITION CONTAINING POLYETHYLENE GLYCOL

The present invention relates to a liquid detergent composition and, in particular, a mild detergent composition suitable for cleansing the skin and hair and comprising a synthetic anionic surfactant, an amphoteric surfactant and a polyethylene glycol.

Traditionally, soap has been an essential component of personal washing compositions both in the solid and liquid form. However, whilst soap based formulations deliver an abundance of lather, soap is considered to be a harsh surfactant which is likely to damage the stratum corneum, i.e the outer layer of the skin, washed with it. Consequently, there has been a move to replace soap, at least partially, in such formulations with synthetic surfactants such as sodium lauryl ether sulphate, commonly referred to as SLES. Formulations based on such anionic surfactants alone tend to produce an abundance of lather during use but the lather is perceived as being of poor quality by the consumer due to its thinness and lack of creaminess. To improve the quality of the lather amphoteric surfactants, and in particular, betaines are commonly added to such compositions as a cosurfactant. Since betaines are mild, their incorporation also leads to improvements in the mildness of the overall composition. As the ratio of amphoteric surfactant to synthetic anionic surfactant is increased so the composition becomes milder however, this is at the expense of the quantity of lather produced during its use.

Attempts to improve lather by increasing the total level of active detergent components in the composition have been unsuccessful. Hence, there has been little exploitation of very mild detergent compositions, particularly in those countries where the quantity and quality of the lather is perceived important by users of such products.

We have now found that for formulations comprising a synthetic anionic surfactant and an amphoteric surfactant in a weight ratio in the range 4:1 to 0.1:1 for optimum mildness, lather can be boosted by the addition of specified polyethylene glycols.

Polyethylene glycol has been suggested as an optional component for detergent compositions comprising a mixture of anionic and amphoteric surfactants and an insoluble nonionic oil such as in WO93/19149. However, in this reference it is mentioned as one of a large group of nonocclusive moisturisers. There is no suggestion that it can be used as a lather booster.

The invention provides an aqueous liquid detergent composition comprising a synthetic anionic surfactant and an amphoteric surfactant in a weight ratio in the range 4:1 to 0.1:1 and a polyethylene glycol having a molecular weight of not more that 100,000.

Anionic Surfactant

Synthetic anionic surfactants are an essential component of the invention as claimed. Suitable materials include fatty acyl isethionates of formula:

$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Other possible anionic detergents include alkyl glyceryl ether sulphate, sulphosuccinates, taurates, sarcosinates, sulphacetates, alkyl phosphate, alkyl phosphate esters and acyl lactylate, alkyl glutamates and mixtures thereof.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_9$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein $R^5$ ranges from $C_9$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_9$–$C_{20}$ alkyl, preferably $C_{12}$–$C_{15}$ alkyl, $R^6$ ranges from $C_1$–$C_4$ alkyl, and M is a solubilising cation.

More preferably the anionic surfactant is an alkyl ether sulphate of formula:

$$R^4O(CH_2CH_2O)_nSO_3M$$

where $R^4$ is an alkyl group of 8 to 22 carbon atoms, n ranges from 0.5 to 10 especially 1.5 to 8, and M is a solubilising cation as before, most preferably the anionic surfactant is sodium lauryl ether sulphate.

Amphoteric Surfactant

Suitable amphoteric surfactants are detergents which have an alkyl or alkenyl group of 7 to 18 carbon atoms and comply with an overall structural formula

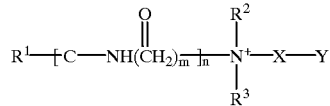

where $R^1$ is alkyl or alkenyl of 7 to 18 carbon atoms $R^2$ and $R^3$ are each independently alkyl, hydroxyalkyl or carboxyalkyl of 1 to 3 carbon atoms M is 2 to 4 n is 0 or 1

X is alkylene of 1 to 3 carbon atoms optionally substituted with hydroxyl, and

Y is —$CO_2^-$ or —$SO_3^-$

They include simple betaines of formula:

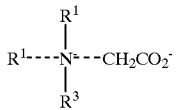

and amido betaines of formula:

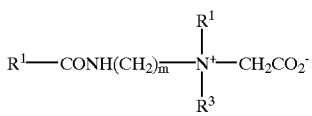

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half of the groups $R^1$ have 10 to 14 carbon atoms. $R^2$ and $R^3$ are preferably methyl.

A further possibility is a sulphobetaine of formula:

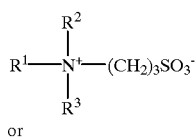

or

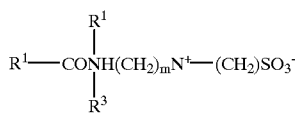

where m is 2 or 3, or variants of these in which —(CH$_2$)$_3$SO$_3^-$ is replaced by

R$^1$, R$^2$ and R$^3$ in these formulae are as defined previously. Amido betaines are most preferred.

The total level of anionic and amphoteric surfactant in the composition according to the invention preferably lies within the range 5 to 50 wt %, most preferably 7 to 35 wt %.

For optimum mildness, the weight ratio of the anionic surfactant to amphoteric surfactant should lie within the range 4:1 to 0.1:1, preferably 3:1 to 0.5:1, more preferably 2:1 to 0.5:1.

The composition may also contain nonionic surfactants. Suitable nonionic surface active agents include alkyl polysaccharides, lactobionamides, ethylene glycol esters, glycerol monoethers, polyhydroxyamides (glucamide), primary and secondary alcohol ethoxylates, especially the C$_{8-20}$ aliphatic alcohols ethoxylated with an average of from 1 to 20 moles of ethylene oxide per mole of alcohol.

Preferably fatty acid soaps are not added to the detergent compositions of the invention. However, if present, they are at a level of not more than 25 wt % based on the level of synthetic anionic surfactant.

Polyethylene Glycol

The polyethylene glycol will have a molecular weight of not more than 100,000; preferably within the range 200 to 25,000 and most preferably within the range 300 to 10,000.

Preferably, the level of polyethylene glycol will be in the range 2 to 40 wt %, most preferably 4 to 30 wt %.

PEG, besides being a lather booster, also effects the mildness of the anionic/amphoteric formulations according to the invention. This effect is only generally noticeable at levels of PEG higher than the minimum required for lather boost i.e. at levels of at least 10 wt % and up 30 wt %.

Although the compositions of the invention may be self-structuring generally they will comprise a structurant and/or a thickener. Suitable materials include swelling clays, for example laponite; fatty acids and derivatives thereof and, in particular, fatty acid monoglyceride polyglycol ethers; cross-linked polyacrylates such as Carbopol (™) (polymers available from Goodrich); acrylates and copolymers thereof, polyvinylpyrrolidone and copolymers thereof; polyethylene imines; nonionic partial triglycerides; natural gums including alginates, guar, xanthan and polysaccharide derivatives including carboxy methyl cellulose and hydroxypropyl guar; propylene glycols and propylene glycol oleates; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates; and mixtures thereof.

Further examples of structurants and thickeners are given in the International Cosmetic Ingredient Dictionary, Fifth Edition, 1993, published by CTFA (The Cosmetic, Toiletry & Fragrance Association), incorporation herein by reference.

Examples of adjuncts which may be added to the composition of the invention include deposition aids and, in particular, anionic polymers such as cationic derivatives of guar gum and quaternary nitrogen-substituted cellulose ether derivatives e.g. guar hydroxylpropyl trimonium chloride, available commercially for example as Jaguar C13S; pearlescers; preservatives such as para-hydroxy benzoate esters; hydrotropes such as alcohols, urea and triethanolamine; antimicrobials such as antioxidants such as butyl hydroxy toluene; bactericides; humectants such as glycerol and sorbitol; sunscreens; plant extracts such as Aloe Vera, witch hazel and elderflower; colourants; and perfumes.

A further group of particularly preferred optional components include moisturising ingredients. Suitable materials include a) hydrocarbons such as petrolatum;
b) higher fatty acids such as those having 8 to 24 carbon atoms;
c) higher fatty alcohols such as those having 8 to 24 carbon atoms;
d) esters such as alkyl lactates;
e) essential oils;
f) lipids such as cholesterol, ceramides, sucrose esters and pseudo-ceramides as described in European Patent Specification No. 556 957 and phospholipids
g) vitamins;
h) derivatives of alpha hydroxy acids such as materials of formula

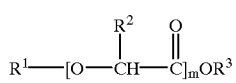

wherein
R$^1$ is C$_p$H$_q$N$_r$O$_s$, where P is 0–20, q is 1–41, r is 0–3, and s is 0–3;
R$^2$ is C$_t$H$_u$ where t is 0–20 and u is 1–41;
R$^3$ is C$_v$H$_w$N$_x$O$_y$ where v is 0–20, w is 1–41, x is 0–3 and y is 0–3 or a metallic, ammonium or alkanolammonium anion and m is 1–10; and
i) mixtures of any of the foregoing components.

The compositions of the invention will generally be pourable liquids or semi-liquids, for example, pastes and will, preferably, have a viscosity in the range 1000 to 200,000 mPas measured at a shear rate of 10s$^{-1}$ and 25° C. in a Haake Rotoviscometer RV20.

The invention will now be illustrated with reference to the non-limiting examples.

EXAMPLES

In the examples
CAPB was cocoamidopropyl betaine ex Henkel
Clay was Laponite XLS (a synthetic hectorite clay) ex Laporte PEG 40 partial diglyceride of hardened castor oil was Cremophor RH410 ex BASF PEG 80 glycery tallowate was Rewoderm LI 48 ex Rewo GmbH SLES was sodium lauryl ether sulphate (3EO) ex Henkel.

All the polyethylene glycols are expressed in terms of their molecular weight and were supplied by BP and BDH.

Example 1

In this comparative example prototypes comprising SLES and CAPB were prepared by heating and mixing the SLES and CAPB using a conventional stirrer.

| Example | SLES/CAPB ratio | Total SLES/CAPB wt % |
|---|---|---|
| 1a | 2:1 | 10 |
| 1b | 2:1 | 20 |
| 1c | 1:1 | 10 |
| 1d | 1:1 | 20 |

The lather volume of these prototypes was measured by the following method in which 20 panellists were used. Each panellist worn a pair of surgical gloves which were turned inside out. The gloved hands were washed with soap to remove the talc and then rinsed with water. 0.5 g of product was applied to a gloved hand of each panellist. Lather was generated by rubbing the hands together for 40 seconds. An inverted funnel connected to a measuring cylinder was placed in a sink of water at ambient temperature. Immediately after the lather had been generated the panellist placed their hands under the funnel, whereby foam floated off into the funnel. The hands were then removed before the position of the measuring cylinder in the sink was adjusted so that the zero point was level with the water level. The amount of foam generated was measured off from the measuring cylinder.

The lather performance of the four prototypes was found to be the same, within experimental error, demonstrating that the lather volume for a given SLES/CAPB ratio cannot be increased merely by increasing the total level of surfactant.

Examples 2–11

In these examples a series of prototype formulations with a SLES/CAPB ratio within the range 2:1 to 1:2 were prepared by heating and mixing the SLES, CAPB and PEG 600 using a conventional stirrer.

Lather volume was measured as described above. The results are given in Table 1, where the lather volume is expressed in terms of significance level over the control which contained no added PEG.

Where lather volume is expressed as '>' this means at 95% significance level.

| | Formulation | | | |
|---|---|---|---|---|
| Example | SLES/CAPB RATIO | TOTAL SLES/CAPB wt % | PEG wt % | Lather Volume Measurement |
| 2 | 1:1 | 10 | 30 | >Control |
| 3 | " | " | 1.0 | =Control |
| Control | " | " | — | — |
| 4 | 1:1 | 20 | 2.5 | >Control |
| 5 | " | " | 5.0 | " |
| 6 | " | " | 10.0 | " |
| 7 | " | " | 15.0 | " |
| Control | " | " | — | — |
| 8 | 2:1 | 10 | 40.0 | >Control |
| 9 | " | " | 50.0 | =Control |
| Control | " | " | — | — |
| 10 | 1:2 | 10 | 5.0 | >Control |
| 11 | " | " | 10.0 | >Control |
| Control | " | " | — | — |

The results demonstrate that it is possible to boost the lather in formulations comprising SLES and CAPB in different weight ratios and total active concentrations. Lather boost was achieved over a wide concentration range of added PEG i.e. from 2.5 to 30 wt %.

Examples 8 and 9 demonstrate that whilst at 40 wt % PEG 600 boosts lather of a formulation comprising SLES and CAPB in a weight ratio of 2:1, when it is added at a higher level of 50 wt % there is no improvement over a composition from which it is absent.

Examples 12–18

In these examples the effect of the molecular weight of the PEG on lather boosting was examined. The amount of PEG added to each prototype formulation was 5 wt %.

| | Formulation | | | |
|---|---|---|---|---|
| Example | SLES/CAPB RATIO | TOTAL SLES/CAPB wt % | PEG Molecular Weight | Lather Volume Measurement |
| Comparative 12 | 2:1 | 10 | — | — |
| 13 | " | " | 1500 | >Control |
| 14 | " | " | 6000 | " |
| 15 | " | " | 10,000 | " |
| 16 | " | " | 100,000 | " |
| Comparative 17 | 2:1 | 20 | 300,000 | =Control |
| | " | " | 1500 | >Control |
| 18 | " | " | 4000 | >Control |

The results demonstrate that PEG of various molecular weights present at a level of 5 wt % delivers a significant improvement in lather volume up to and including a molecular weight of 100,000. PEG with a molecular weight of 300,000 did not provide a lather boost and, furthermore, the formulation containing this material was unacceptable as it was perceived as making the skin feel slimy during use.

Examples 19–22

In these examples the effect of PEG 600 or PEG 4000 on lather was examined in a variety of fully formulated products. Products were prepared by mixing the surface active agents, PEG and glycerol at elevated temperatures using an order of addition which avoided the formation of viscous phases. Thereafter prehydrated Laponite was injected into the blend. After addition of minors the blend was cooled and emptied from the mixer.

The lather properties of these products were measured as described previously and found to be superior to those products which did not contain PEG.

TABLE 2

| Component wt % | Example 19 | Example 20 | Example 21 | Example 22 |
|---|---|---|---|---|
| SLES 3 EO | 10.0 | 8.0 | 12.0 | 12.0 |
| CAPB | 10.0 | 5.0 | 7.5 | 7.5 |
| Glycerol | 5.0 | 5.0 | 5.0 | 5.0 |
| PEG 600 | 5.0 | 5.0 | — | — |
| PEG 4000 | — | — | 5.0 | 5.0 |
| PEG-80 glycerol tallowate | 3.0 | 5.0 | 7.5 | — |
| PEG 40 partial diglyceride of hardened castor oil | — | 3.0 | 3.0 | 3.0 |
| Propan-1, 2-diol | 3.0 | — | — | — |
| Clay | 0.6 | 1.5 | 1.5 | 1.5 |
| Minors + Water | to 100 | to 100 | to 100 | to 100 |

Example 23

In this example a number of compositions were assessed for mildness using a zein test generally as described by Gotte, Proc. Int. Cong. Surface Active Subs., 4th Edition, Brussels, 3, 89–90 (1964). The test determines the amount of amino acid solubilised from zein under specified conditions. The solubilised material is determined by a nitrogen assay. The results were as follows:

| SLES/CAPB = 1:1 ratio | |
|---|---|
| Total SLES/CAPB = 10 wt % | |
| % PEG 600 | Zein Score % Nitrogen |
| 0 | 0.21 |
| 5 | 0.20 |
| 10 | 0.18 |
| 20 | 0.14 |
| 30 | 0.15 |
| 35 | 0.14 |

| SLES/CAPB = 2:1 | | |
|---|---|---|
| Total SLES/CAPB = 10 wt % | | |
| PEG Mwt | % PEG | Zein Score |
| — | 0 | 0.28 |
| 600 | 20 | 0.23 |
| 4000 | 15 | 0.19 |
| 100,000 | 5 | 0.29 |

(*all scores were corrected for the N content of CAPB)

The results demonstrate that addition of PEG at levels of 10% wt or greater improves mildness, as determined by zein score.

We claim:

1. An aqueous liquid detergent composition consisting of a synthetic anionic surfactant and an amphoteric surfactant in a weight ratio within the range 4:1 to 0.1:1 and from 10% to 40% by weight of a polyethylene glycol having a molecular weight of 200 to not more than 100,000.

2. A composition according to claim 1 wherein the total level of synthetic anionic surfactant and amphoteric surfactant lies within the range 5 to 50 wt %.

3. A composition according to claim 1 wherein the ratio of synthetic anionic surfactant to amphoteric surfactant lies within the range 3:1 to 0.5:1.

4. A composition according to claim 1 wherein the polyethylene glycol has a molecular weight within the range 200 to 25,000.

* * * * *